(12) United States Patent
Schaffer

(10) Patent No.: US 9,789,360 B1
(45) Date of Patent: Oct. 17, 2017

(54) APPARATUS FOR MONITORING EXERCISE EFFICIENCY AND USAGE

(71) Applicant: Gary L. Schaffer, Newport Coast, CA (US)

(72) Inventor: Gary L. Schaffer, Newport Coast, CA (US)

( * ) Notice: Subject to any disclaimer, the term of this patent is extended or adjusted under 35 U.S.C. 154(b) by 0 days.

(21) Appl. No.: 14/630,405

(22) Filed: Feb. 24, 2015

(51) Int. Cl.
| A63B 71/00 | (2006.01) |
| A63B 21/072 | (2006.01) |
| A63B 21/075 | (2006.01) |
| A63B 24/00 | (2006.01) |
| A63B 21/00 | (2006.01) |
| A63B 53/04 | (2015.01) |

(52) U.S. Cl.
CPC ...... *A63B 24/0062* (2013.01); *A63B 21/0004* (2013.01); *A63B 21/072* (2013.01); *A63B 21/0722* (2015.10); *A63B 21/0724* (2013.01); *A63B 2053/0441* (2013.01)

(58) Field of Classification Search
USPC .......................................................... 482/1, 8
See application file for complete search history.

(56) References Cited

U.S. PATENT DOCUMENTS

| 3,271,030 A | * | 9/1966 | Mueller | A63B 69/0091 |
| | | | | 473/423 |
| 3,612,460 A | * | 10/1971 | Smith | G09F 7/18 |
| | | | | 248/230.9 |
| 4,938,476 A | * | 7/1990 | Brunelle | A63B 23/0244 |
| | | | | 340/573.7 |
| 5,300,921 A | * | 4/1994 | Hoch | A61B 5/1121 |
| | | | | 273/DIG. 17 |
| 5,441,269 A | * | 8/1995 | Henwood | A63B 69/3685 |
| | | | | 473/220 |
| 5,692,965 A | * | 12/1997 | Nighan, Jr. | A63B 69/3614 |
| | | | | 362/102 |
| 5,792,001 A | * | 8/1998 | Henwood | A63B 69/3685 |
| | | | | 473/220 |
| 5,873,789 A | * | 2/1999 | Torriano | A63B 69/3614 |
| | | | | 362/259 |
| 5,980,393 A | * | 11/1999 | Molinaroli | A63B 69/3614 |
| | | | | 362/259 |
| 7,878,917 B2 | * | 2/2011 | Johnson | A63B 69/3685 |
| | | | | 473/220 |
| 7,927,252 B1 | * | 4/2011 | Jeffrey | A63B 24/0003 |
| | | | | 434/247 |
| 7,963,886 B1 | * | 6/2011 | Schwinn | A63B 21/078 |
| | | | | 482/5 |
| 8,436,737 B1 | * | 5/2013 | Trout | A61B 5/1116 |
| | | | | 340/573.1 |

(Continued)

*Primary Examiner* — Sundhara Ganesan
*Assistant Examiner* — Shila Jalalzadeh Abyan
(74) *Attorney, Agent, or Firm* — Rutan & Tucker, LLP

(57) ABSTRACT

An embodiment of an exercise monitoring apparatus is shown. Herein, the exercise monitoring apparatus comprises a casing, a fastening member, a first laser device and a second laser device. The first laser device is oriented so that, when actuated, the device outwardly projects a first light beam in a direction substantially perpendicular to a top surface of the casing. The first light beam visually produces a line of light. The second laser device is oriented so that, when actuated, the device outwardly projects a second light beam in a direction substantially perpendicular to one of the sidewalls of the casing and substantially perpendicular to the first light beam.

18 Claims, 3 Drawing Sheets

(56) References Cited

U.S. PATENT DOCUMENTS

| | | | | |
|---|---|---|---|---|
| 8,602,945 | B1* | 12/2013 | Haubrich | A63B 71/0622 |
| | | | | 482/1 |
| 9,211,439 | B1* | 12/2015 | Pedenko | A63B 24/0006 |
| 2007/0042875 | A1* | 2/2007 | Arginsky | A63B 25/08 |
| | | | | 482/77 |
| 2008/0200274 | A1* | 8/2008 | Haag | A63B 69/3614 |
| | | | | 473/222 |
| 2010/0156625 | A1* | 6/2010 | Ruha | A61B 5/02055 |
| | | | | 340/539.12 |
| 2012/0165165 | A1* | 6/2012 | Iankov | A63B 71/0608 |
| | | | | 482/106 |
| 2014/0045660 | A1* | 2/2014 | Murray | A63B 21/0724 |
| | | | | 482/106 |
| 2014/0121075 | A1* | 5/2014 | Brown | A63B 21/026 |
| | | | | 482/106 |
| 2015/0367176 | A1* | 12/2015 | Bejestan | G06F 19/3481 |
| | | | | 482/9 |

* cited by examiner

APPARATUS FOR MONITORING EXERCISE EFFICIENCY AND USAGE

1. FIELD

Embodiments of the disclosure relate to the field of fitness equipment, namely exercise or sporting equipment. More specifically, one embodiment of the disclosure relates to electronics that is integrated within or attached to the fitness equipment to assist in monitoring proper or optimal usage of that equipment.

2. GENERAL BACKGROUND

Over the last few decades, the medical profession has widely considered that persons who exercise regularly experience better health over their lifetimes than sedentary persons. Exercise stretches and contracts muscles and stimulates breathing thereby improving blood circulation and lung function. Exercise has also been shown to improve insulin sensitivity for healthy persons and those with non-insulin dependent diabetes. Weight-bearing exercises also strengthen bones and may help decrease the risk of osteoporotic fractures.

However, when performed improperly, certain exercises may be harmful to a person. For example, when lifting weights, twisting and turning while lifting can lead to injury, such as a herniated disk and a lifetime of back pain. In fact, non-optimal usage of this equipment may restrict future motion due to a lack of full extension of muscles and supporting muscular skeletal systems. In order to ensure that an exercise regimen is performed properly, a person may hire a trainer to watch the exercises being conducted and correct deviations in proper form. However, in many situations, reliance on a trainer is costly and inconvenient as it requires a person's exercise regimen to also comply with the trainer's schedule. The same issues are also present for person's practicing a sports activity, where personal coaches are hired to improve form and effectiveness in the use of certain sporting equipment such as tennis rackets, golf clubs and the like.

BRIEF DESCRIPTION OF THE DRAWINGS

Embodiments of the invention are illustrated by way of example and not by way of limitation in the figures of the accompanying drawings, in which like references indicate similar elements and in which.

DETAILED DESCRIPTION

Figure 1:
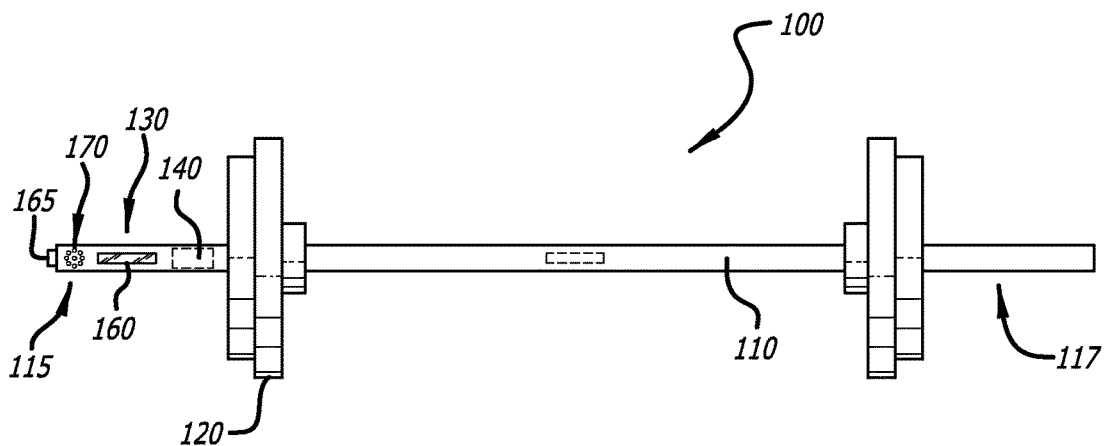
FIG. 1 is an exemplary diagram of sporting equipment deploying exercise monitoring logic integrated within the sporting equipment.

Various embodiments of the disclosure relate to fitness equipment implemented with exercise monitoring logic that assists the user in monitoring that the fitness equipment is being used properly to maximize performance and/or medicinal benefits. As an optional feature, the exercise monitoring logic may monitor parameters in use of the fitness equipment (e.g., particular exercise or practice regimen performed and data associated with such regimen including number of repetitions, weight, angular ranges of motion performed for that regimen, etc.). According to one embodiment of the disclosure, integrated into a portion of the fitness equipment or implemented as a separate unit that is removably attached to the fitness equipment, the exercise monitoring logic is configured to monitor for deviations in positioning of the fitness equipment that are more than a prescribed threshold. When such a deviation occurs, the exercise monitoring logic notifies the user through one or more visual queues and/or auditory sound.

According to one embodiment, the exercise monitoring logic comprises at least a first laser device and a second laser device. When in operation, the first laser device is oriented to enable the user (or another person or specific equipment) to monitor planar movement of the fitness equipment. When in operation, the second laser device is oriented to enable the user to monitor rotational movement of the fitness equipment, which may be useful for analysis of thoracic rotation range of motion for example. Each of these lasers may be selectively actuated by a controller to either (i) output continuous light beams, or in response to significant deviations from expected planar or rotational movement, (ii) output laser light patterns or colors to identify this deviation.

As this invention is susceptible to embodiments of many different forms, it is intended that the present disclosure is to be considered as an example of the principles of the invention and not intended to limit the invention to the specific embodiments shown and described.

I. Terminology

In the following description, certain terminology is used to describe aspects of the invention. For example, in certain situations, the terms "logic" or "unit" are representative of hardware, firmware and/or software that is configured to perform one or more functions. As hardware, logic (or unit) may include circuitry having data processing or data storage functionality. Examples of such processing circuitry may include, but is not limited or restricted to a controller in the form of one or more processors, one or more processor cores, a programmable gate array, a microcontroller, an application specific integrated circuit, or combinations thereof; a receiver, transmitter and/or transceiver circuitry; combinatorial logic; or combinations of one or more of the above circuitry. An example of storage circuitry provides semiconductor memory, a solid-state drive, or the like.

Logic (or unit) may be in the form of one or more software modules, such as executable code in the form of an executable application, an application programming interface (API), a subroutine, a function, a procedure, an applet, a servlet, a routine, source code, object code, a shared library/dynamic load library, or one or more instructions. These software modules may be stored in any type of a suitable non-transitory storage medium, or transitory storage medium (e.g., electrical, optical, acoustical or other form of propagated signals such as carrier waves, infrared signals, or digital signals). Examples of a "non-transitory storage medium" may include, but are not limited or restricted to a programmable circuit; non-persistent storage such as volatile memory (e.g., any type of random access memory "RAM"); persistent storage such as non-volatile memory (e.g., read-only memory "ROM", power-backed RAM, flash memory, phase-change memory, etc.), a solid-state drive, hard disk drive, an optical disc drive, or a portable memory device; and/or a semiconductor memory. As firmware, the executable code is stored in persistent storage.

The term "fitness equipment" generally refers to any exercise or sporting equipment that may be used by a person as part of an exercise or practice regimen. Examples of fitness equipment may include, but are not limited or restricted to various types of exercise equipment including a barbell, a dumbbell, a weighted bar, and/or an exercise bar (e.g., hip hinge dowel, etc.). Of course, it is contemplated that the invention may be applicable to other types of equipment, including sporting equipment such as a tennis racket for example.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

II. General Architectures

Referring to FIG. 1, an exemplary block diagram of fitness equipment 100 with integrated exercise monitoring logic 130 is shown. Herein, the fitness equipment 100 is exercise equipment in the form of a weight set including a cylindrical element (e.g., a lift bar 110) and weight plates 120 that are secured on both ends of the lift bar 110. The exercise monitoring logic 130 is at least partially integrated within a compartment formed by inner surfaces of the lift bar 110, such as an inner compartment towards a first end 115 of the lift bar 110 or centrally between the first end 115 and a second end 117 as optionally shown.

As shown, the exercise monitoring logic 130 comprises control logic 140, which monitors the positioning of the lift bar 110 and is communicatively coupled to one or more sensory components 150, such as visual monitoring components that may include a first laser device 160 and/or a second laser device 165, and/or audible monitoring logic including an audio output unit 170 (e.g., a digital-to-analog "D/A" converter, one or more speakers, etc.). Although not shown, it is contemplated that the exercise monitor logic 130 may include an internal power source (e.g., battery, rechargeable battery via a power connector in the lift bar 110, photocell, etc.).

According to this embodiment of the disclosure, the control logic 140 is configured to monitor for longitudinal deviations in movement of the lift bar 110 (e.g., deviations greater than a prescribed angular offset from an expected vertical path of travel of the lift bar 110) as well as for lateral deviations in movement of the lift bar 110 (e.g., tilting of the lift bar 110 by a prescribed angular offset from horizontal).

It is contemplated that, after activation of the exercise monitoring logic 130, the lift bar 110 may be adjusted or moved into position prior to commencing an exercise regimen. To avoid erroneous reporting of improper movement of the lift bar 110, the control logic 140 may be configured to continuously monitor and report longitudinal and/or lateral deviations (i) after a prescribed time from activation of the control logic 140, (ii) after an initial substantial deviation from a current position to account for placement of the lift bar 110 into a start position, and/or (iii) after detecting a repeated a path of travel (e.g., after second repetition of downward/upward movement of the lift bar 110).

The reporting of movement deviations may be conducted by the control logic 140 providing digitized audio that undergoes digital-to-analog conversion for playback over the one or more speakers 172. The digitized audio may be generated by the control logic 140 or may be pre-stored audio that is fetched from a data store. According to one embodiment of the disclosure, the audio may be a single audible tone or may be a series of audible tones. Alternatively, the audio may include pre-stored dialog that describes the movement deviation detected and/or provides verbal instructions for correcting the movement deviation.

In addition to or in lieu of audio reporting, the control logic 140 may report movement deviations by altering the light produced from the first laser device 160 or the second laser device 165. For instance, the pattern of the light may be altered (e.g., change from continuous light beam to a flashing light beam, change from one continuous light beam to discontinuous segments of light beams, etc.). The pattern of the light may also be altered by changing the color of the light, where different colors may represent different degrees of movement deviation (e.g., "orange" represents a first amount of deviation, "red" represents a second (and more substantial) amount of deviation, etc.).

According to one embodiment of the disclosure, the sensory components 150 may be selectively actuated by the control logic 140, so that all, some, or none of these sensory components 150 are in operation during use of the fitness equipment 100. The actuation of the sensory components 150 may be in response to an event and may be delayed from activation of the exercise monitoring logic 130. For instance, activation of the control logic 140 of the exercise monitoring logic 130 may occur upon depressing a power-on button, but one or more of the sensory components 150 may be actuated a predetermined period of time subsequent to activation of the control logic 140. As another example, it is contemplated that depressing a power-on button activates the control logic 140 of the exercise monitoring logic 130, but one or more of the sensory components 150 are actuated upon the user placing his or her hands at particular locations on the lift bar 110 that close the circuit including the sensory components 150.

According to this embodiment of the disclosure, the sensory components 150 are used to provide information to the user as to improper usage of the fitness equipment 100. For instance, the first laser device 160 operates as a line laser which, when actuated, outwardly projects a light beam that visually produces a line of light. When oriented facing upward on the lift bar 110, the first laser device 160 projects the light beam toward a ceiling. This allows the user, when bench pressing for example, to visually see a vertical plane including the first laser device 160 that represents a desired path of movement for the fitness equipment 100.

For instance, when the first laser device 160 is actuated and, when the lift bar 110 is placed in a first (lowered) position, a light beam is projected upward and the line of light is visible on the ceiling. Thereafter, as the user lowers the lift bar 110 downward or raises the lift bar 110 upward, the first laser device 160 continues to project the light beam toward the ceiling. Therefore, during the raising or lowering of the lift bar 110, any movement of the lift bar 110 in a longitudinal direction (e.g., deviations from a vertical path of travel) may be visually detected by the user. Such detection may occur by the user noticing longitudinal movement of the line of light displayed on the ceiling. Alternatively, such detection may be through adjustment of the light pattern and/or audio generated by the control logic 140.

Similarly, when the second laser device 165 is actuated and, when the lift bar 110 is tilted from horizontal by at least a prescribed angular offset, a point of light from the second laser device 165 is projected in a direction substantially perpendicular to the direction of light produced from the first laser device 160. Thereafter, as the user lowers or raises one end of the lift bar 110, the second laser device 165 projects a light beam above or below a horizontal plane including the lift bar 110. For instance, where the first end 115 of lift bar 110 including the second laser device 165 is lowered below the second end 117 by a prescribed angular offset, the second laser device 165 projects a point laser at a position lower than the first end 115 of the lift bar 110.

Although not shown, it is contemplated that the exercise monitoring logic 130 may comprise a keypad that is accessible to the user. Operating as an input device, the keypad may be used to identify upcoming usage of the fitness equipment 100 (e.g., a selected exercise from which preloaded heuristics may be loaded into the control logic 140 to assist in identifying movements of the fitness equipment 100 that are to be monitored, the number of sets associated with a particular exercise, etc.).

Figure 2:
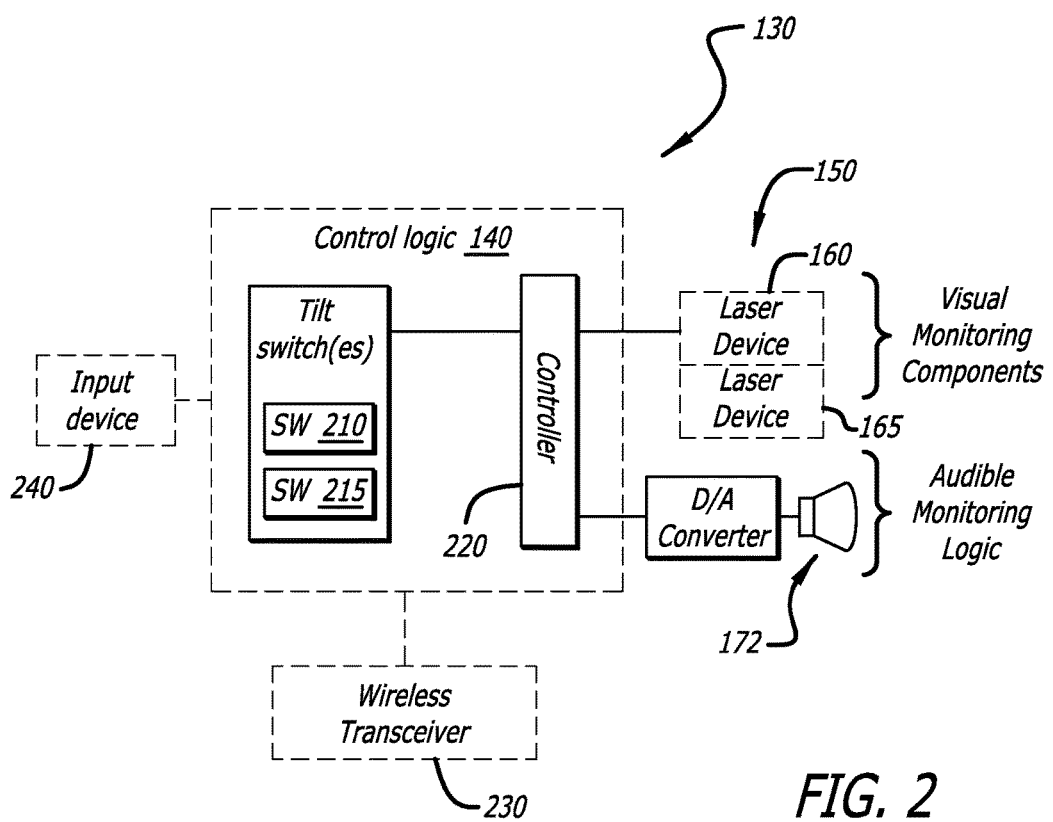
FIG. 2 is a first exemplary embodiment of the exercise monitoring logic of FIG. 1.

Referring now to FIG. 2, a first exemplary embodiment of the exercise monitoring logic 130 of FIG. 1 is shown. Herein, the exercise monitoring logic 130 comprises control logic 140 and/or sensory monitoring components 150. The control logic 140 monitors the two-dimensional orientation of the exercise monitoring logic 130 and, upon detecting a deviation in orientation that exceeds a prescribed threshold, may issue a notification to the user. As described above, the monitoring period may commence a predetermined time after activation (or reset) of the control logic 140 or may commence upon identification of a start of an exercise or practice regimen to be monitored.

In response to detecting a deviation in orientation along the horizontal (x-axis) direction that exceeds a prescribed threshold, the control logic 140 may signal the sensory monitoring components 150 to provide a notification to the user. This notification may include altering visible light patterns produced by the first laser device 160 or generating audio for playback via one or more speakers 172. Similarly, in response to detecting deviations in orientation in the vertical (y-axis) direction, such as tilting exceeds a prescribed threshold, the control logic 140 may signal the sensory monitoring components 150 to provide a notification to the user. As the light beam from the second laser device 165 produces a different visual image (e.g., a point of light in lieu of a line of light), the type notification may be the same or differ slightly (e.g., altering the pattern or color of the visible point of light produced by the second laser device 165 and/or generating audio for playback via one or more speakers 172).

More specifically, the control logic 140 comprises one or more tilt switches 200 and a controller 220. The tilt switch(es) 200 include a first tilt switch 210, which is adapted to monitor for longitudinal (x-axis) deviations in movement of the exercise monitoring logic 130. These longitudinal deviations denote changes from a vertical path of travel by a first prescribed angular offset (e.g. 5° from vertical, 10° from vertical, etc.). The tilt switch(es) 200 may further include a second tilt switch 215, which is adapted to monitor for lateral (y-axis) deviations in movement. These lateral deviations denote changes from horizontal by a second prescribed angular offset (e.g., tilting that is 5° from horizontal, 10° from horizontal, etc.). The first and second prescribed angular offsets may be the same or different from each other.

As an optional feature, the exercise monitoring logic 130 comprises a wireless transceiver 230, which is communicatively coupled to the controller 220. The wireless transceiver 230 enables the controller to upload data with respect to usage of the fitness equipment. This data may include heuristics that identifies proper and/or improper usages of the fitness equipment (e.g., the number of repetitions with longitudinal deviations for a given exercise or practice, the number of repetitions with lateral deviations for a given exercise or practice, percentage of proper or improper repetitions, etc.). The wireless transceiver 230 further enables the controller 220 to download software updates.

As another optional feature, the exercise monitoring logic 130 comprises an input device 240 such as a keypad. The input device 240 enables the user to identify a particular exercise or practice drill that is to be conducted by the user. This information may be used by the controller 220 to select a particular program to assist in accurately monitoring usage of the fitness equipment 100. Additionally, the input device 240 may also be used by a training assistant to mark proper range of motion for the desired exercise (e.g., when the equipment hits a certain position, the controller 220 to generate an audible signal via the audio output unit 170.

Figure 3:
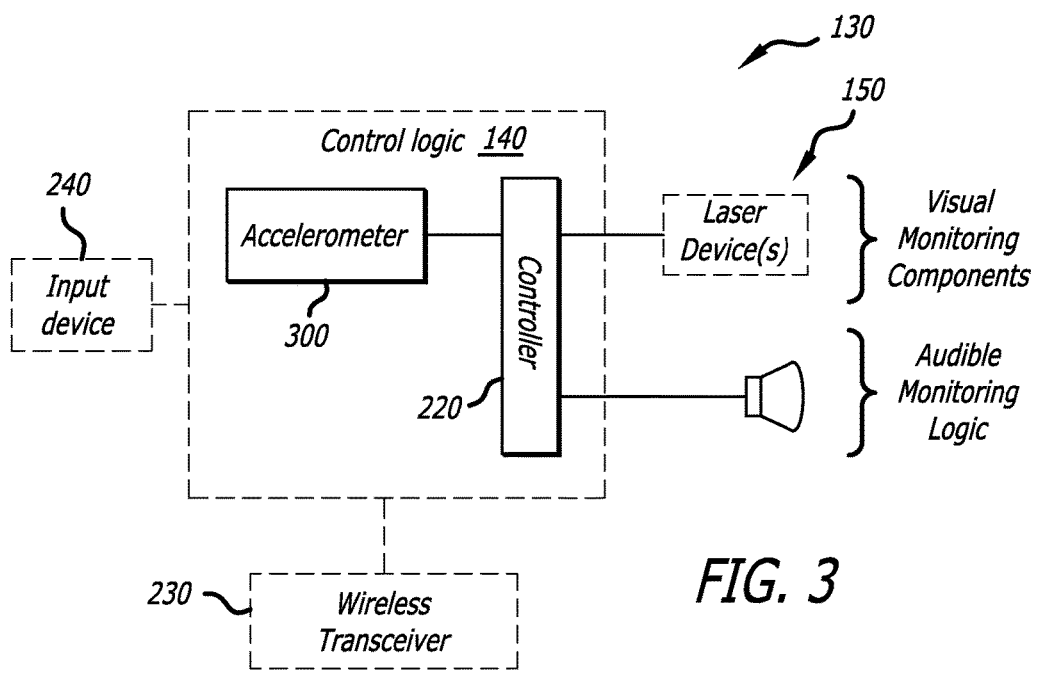
FIG. 3 is a second exemplary embodiment of the exercise monitoring logic of FIG. 1.

Referring to FIG. 3, a second exemplary embodiment of the exercise monitoring logic 130 of FIG. 1 is shown. Herein, the exercise monitoring logic 130 comprises control logic 140 and/or sensory monitoring components 150. However, unlike FIG. 2, the control logic 140 monitors the three-dimensional orientation of the exercise monitoring logic 130 through an accelerometer 300. The accelerometer 300 detects magnitude and direction, which may be used to sense orientation through direction of weight changes. Upon detecting deviations in orientation that exceeds a prescribed threshold in any of the three dimensions, the control logic 140 issues a notification to the user, as described above.

Figure 4A:
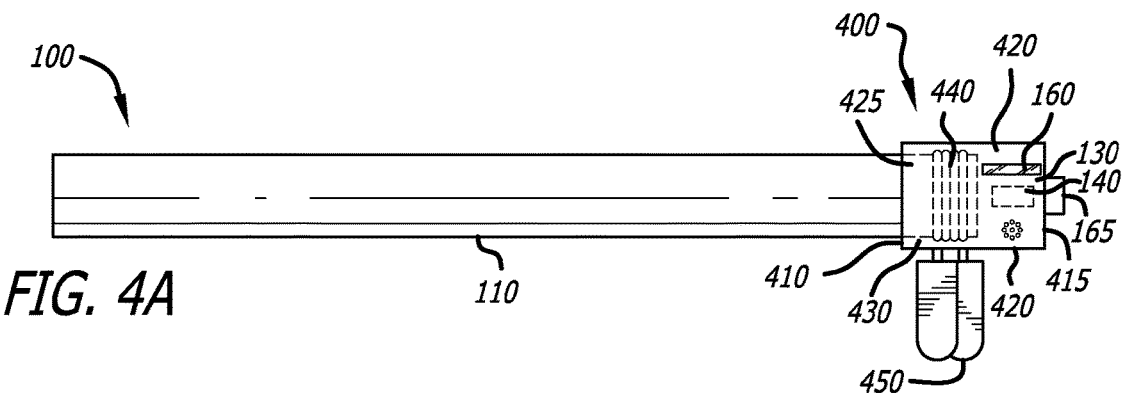
FIGS. 4A-4B are exemplary plan views of sporting equipment deploying a first embodiment of an attachment implemented with exercise monitoring logic of FIG. 2 or 3.
Figure 4B:
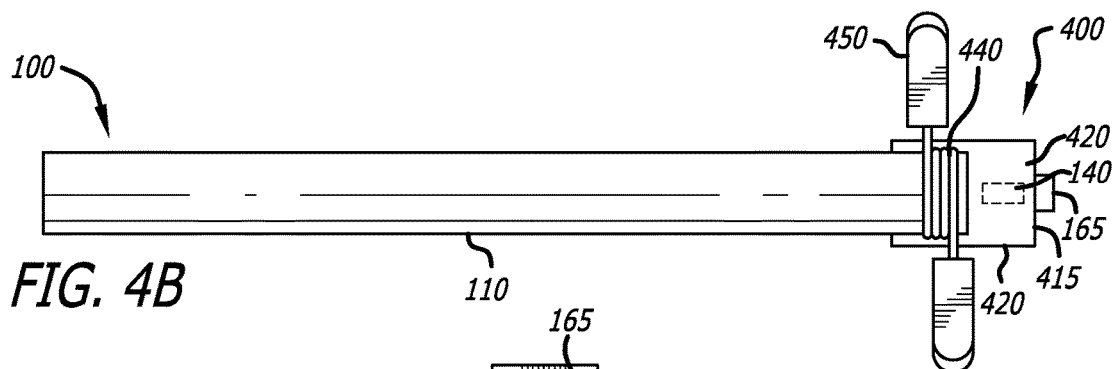

FIGS. 4A and 4B are exemplary plan views of fitness equipment deploying a first embodiment of an attachment implemented with the exercise monitoring logic 130 of FIG. 2 or 3. One embodiment of the attachment is a spring collar 400 deployed to retain weight plates on a lift bar. Herein, the spring collar 400 comprises a casing 410, which at least partially houses a fastening member (e.g., spring 440) and the exercise monitoring logic 130. The casing 410 comprises a top surface 415 situated at a first end, sidewalls 420 extending from a periphery of the top surface 415, and a recess 425 formed by at least a portion of the sidewalls 420 and an open second end of the casing 410.

Positioned between a bottom surface of the recess 425 (not shown) and the top surface 415 of the casing 410 is a compartment 430 that houses the spring 440 and at least a portion of the exercise monitoring logic 130. The spring 440 is wounded coil having a first diameter when the spring 440 is placed in a first state and a second diameter when the spring 440 is placed in a second state. A pair of handles 450 are placed at the end of the spring 440 so that, when the handles 450 are moved closer to each another (e.g., spring 440 is placed in the second state), the diameter of the coil increases. Upon releasing the handles 440, the diameter of the coil decreases and the spring 440 returns to the first state.

Figure 4C:
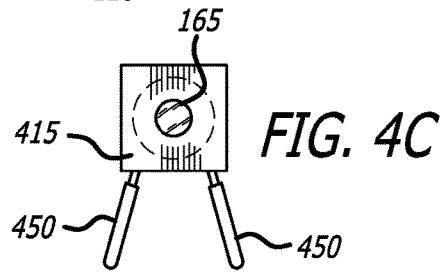
FIG. 4C is an exemplary perspective view of the attachment of FIGS. 4A-4B.

The compartment 430 contains the control logic 140 of the exercise monitoring logic 130; however, the first laser device 160 positioned along one of the sidewalls 420 of the casing 410. This allows the first laser device 160 to be oriented facing upward. The second laser device 165 of the exercise monitoring logic 130 is positioned to direct a light beam in a direction perpendicular to the top surface 415 of the casing 410. As shown, the second laser device 165 may protrude from the top surface 415 as shown in FIG. 4C.

Figure 5:
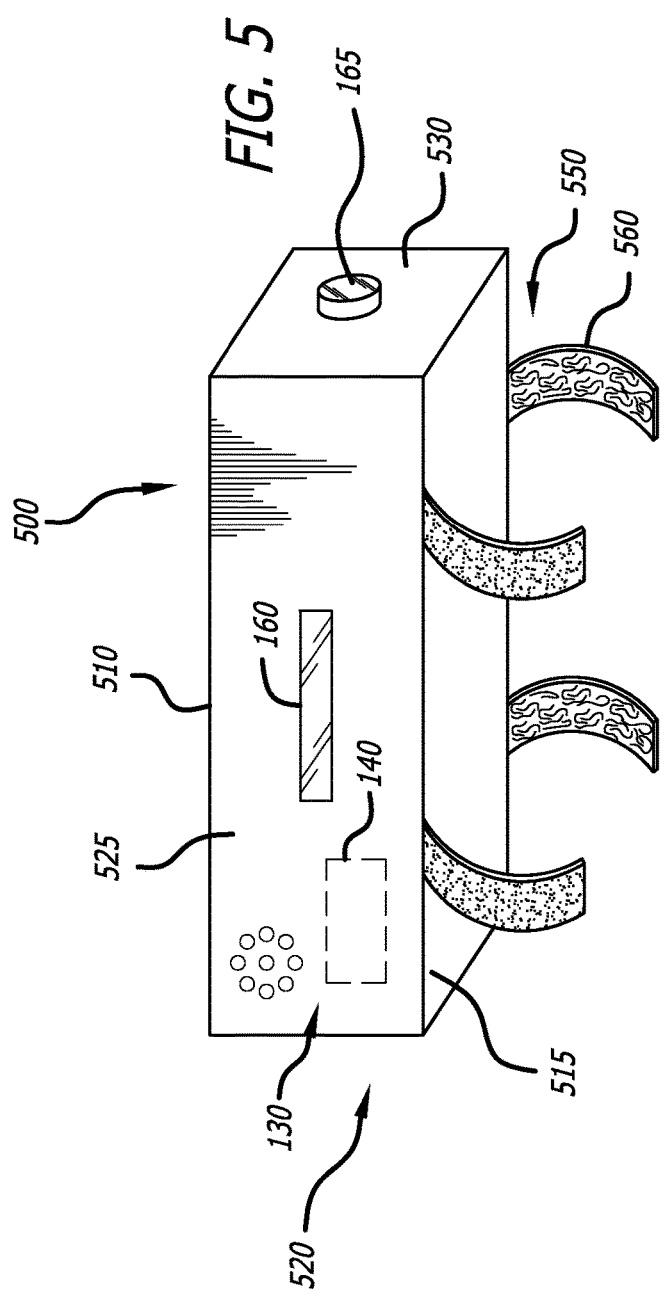
FIG. 5 is an exemplary perspective diagram of a second embodiment of an attachment implemented with exercise monitoring logic of FIG. 2 or 3.

FIG. 5 is an exemplary perspective diagram of a second embodiment of an attachment implemented with exercise monitoring logic of FIG. 2 or 3. Herein, one embodiment of the attachment comprises a casing 500 with a fastening member 550 to securely attach the casing 500 to the fitness equipment 100 (e.g., hip hinge dowel).

Figure 6:
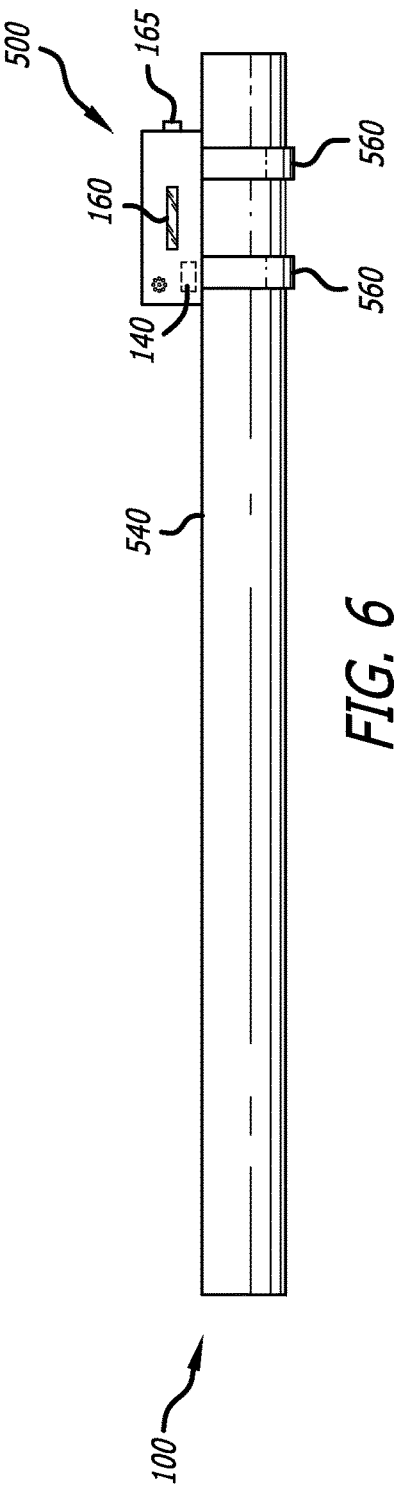
FIG. 6 is an exemplary diagram of sporting equipment deploying the attachment of FIG. 5.

According to this embodiment, the fastening member 550 comprises a pair of Velcro® straps 560, although other fastening mechanisms may be used. The casing 500 is made of hardened plastic to protect portions of the exercise monitoring logic 130 deployed within the casing 500. The casing 500 comprises a top surface 510, a bottom surface 515, and a plurality of perimeter surfaces 520 including a first perimeter surface 525 and a second perimeter surface 530 that is immediately adjacent to the first perimeter surface 525. When attached to the fitness equipment 100, as shown in FIG. 6, the bottom surface 515 is positioned adjacent to and in contact with a surface 540 of the fitness equipment 100.

The casing 500 contains the control logic 140 of the exercise monitoring logic 130; however, the first laser device 160 may be positioned along the first perimeter surface 525 of the casing 500. This allows the first laser device 160 to be oriented facing upward. The second laser device 165 of the exercise monitoring logic 130 is positioned to direct a light beam in a direction perpendicular to the second perimeter surface 530 of the casing 500.

In the foregoing description, the invention is described with reference to specific exemplary embodiments thereof. It will, however, be evident that various modifications and changes may be made thereto without departing from the broader spirit and scope of the invention as set forth in the appended claims.

What is claimed is:

1. An exercise monitoring apparatus comprising:
   a casing;
   a fastening member coupled to the casing, the fastening member configured to attach the casing to an exercise equipment; and
   exercise monitoring logic at least partially contained in the casing, the exercise monitoring logic comprises
   (i) one or more tilt switches,
   (ii) one or more sensory elements including at least a first laser device that, when actuated, outwardly projects a planar light beam and produces a visual line of light representing a prescribed path of travel, and
   (iii) a controller communicatively coupled to the one or more tilt switches and the one or more sensory elements, the controller configured to generate a signal to the one or more sensory elements to emit an alert in response to the one or more tilt switches detecting a deviation in longitudinal or lateral movement of the exercise equipment by at least a prescribed angular offset from the prescribed path of travel.

2. The exercise monitoring apparatus of claim 1, wherein the one or more sensory elements further comprise a second laser device that, when actuated, outwardly projects a point of light in a direction substantially perpendicular to the direction of the planar light beam produced from the first laser device.

3. The exercise monitoring apparatus of claim 1, wherein the first laser device is oriented to outwardly project the planar light beam that produces the visible line of light for monitoring lateral movement of the exercise equipment along a vertical path.

4. The exercise monitoring apparatus of claim 1, wherein the controller is configured to generate the signal to the one or more sensory elements to emit the alert in response to both (i) the deviation in longitudinal or lateral movement of the exercise equipment by at least the prescribed angular offset and (ii) the deviation occurs after a prescribed time from activation of the exercise monitoring logic.

5. The exercise monitoring apparatus of claim 1, wherein the one or more sensory elements further comprise at least one digital-to-analog converter in communication with the controller and a speaker coupled to the digital-to-analog converter and the signal being stored audio that is converted by the digital-to-analog converter into playback audio that provides verbal instructions to correct the deviation.

6. The exercise monitoring apparatus of claim 1,
   wherein the exercise equipment comprises a cylindrical bar; and
   wherein the fastening member comprises a coiled spring having a first diameter when placed in a first state and securely coupled to the cylindrical bar and having a second diameter when placed in a second state that allow removal of the cylindrical bar.

7. The exercise monitoring apparatus of claim 1 further comprising a keypad configured to provide information to the controller that identifies a particular exercise to be conducted and selects a proper range of motion of the exercise equipment, including the longitudinal or lateral movement of the exercise equipment.

8. An exercise monitoring apparatus comprising:
   a casing including a top surface, a bottom surface and a plurality of sidewalls;
   a fastening member coupled to the casing, the fastening member configured to attach the casing to a fitness equipment;
   a first laser device being oriented so that, when actuated, outwardly projects a planar, first light beam in an upward direction substantially perpendicular to the top surface of the casing, the planar, first light beam being projected from the first laser device to produce a visible line of light;
   a second laser device being oriented so that, when actuated, outwardly projects a second light beam in a direction substantially perpendicular to one of the sidewalls of the casing and to the planar, first light beam;
   one or more tilt switches; and
   a controller communicatively coupled to the one or more tilt switches, the first laser device and the second laser device, the controller configured to generate a signal to at least one of the first laser device or second laser device in response to deviation in movement of the fitness equipment detected by the one or more tilt switches.

9. The exercise monitoring apparatus of claim 1, wherein the controller to generate the signal to the first laser device to emit the alert that includes altering a pattern of the planar light beam emitted by the first laser device.

10. The exercise monitoring apparatus of claim 9, wherein the altered pattern of the planar light beam emitted by the first laser device includes a change of the planar light beam to produce the visible line of light from a continuous line of light to a series of disconnected segments of light.

11. The exercise monitoring apparatus of claim 10, wherein the change of the color of the planar light beam includes (i) a change of color from a first color to a second color to identify a first degree of deviation in the longitudinal or lateral movement of the exercise monitoring logic and (ii) a change of color from the first color to a third color to identify a second degree of deviation in the longitudinal or lateral movement of the exercise monitoring logic.

12. The exercise monitoring apparatus of claim 9, wherein the altered pattern of the planar light beam emitted by the first laser device includes a change of a color of the planar light beam.

13. The exercise monitoring apparatus of claim 8, wherein the controller configured to generate a signal to the first laser device to alter a representation of the planar, first light beam produced by the first laser device in response to the controller detecting, from signaling from the one or more tilt switches, a deviation in longitudinal movement of the fitness equipment by a prescribed angular offset.

14. The exercise monitoring apparatus of claim 13, wherein the controller configured to generate the signal to the first laser device to emit the alert that includes altering a pattern of the planar light beam emitted by the first laser device, the altered pattern of the planar light beam emitted by the first laser device includes either (i) a change of the planar light beam to produce the visible line of light from a continuous line of light to a series of disconnected segments of light or (ii) a change of a color of the planar light beam.

15. The exercise monitoring apparatus of claim 14, wherein the change of the color of the planar light beam includes (i) a change of color from a first color to a second color to identify a first degree of deviation in the longitudinal or lateral movement of the fitness equipment and (ii) a change of color from the first color to a third color to identify a second degree of deviation in the longitudinal or lateral movement of the exercise monitoring logic fitness equipment, where the second degree of deviation is different than the first degree of deviation.

16. The exercise monitoring apparatus of claim 8, wherein the controller configured to generate a signal to the second laser device to alter a representation of the second light beam produced by the second laser device in response to the controller detecting, from signaling from the one or more tilt switches, a deviation in lateral movement of the fitness equipment by a prescribed angular offset.

17. The exercise monitoring apparatus of claim 8, wherein the controller configured to generate (a) a first signal to the first laser device to alter a representation of the first light beam produced by the first laser device in response to the controller detecting, from signaling from the one or more tilt switches, a deviation in longitudinal movement of the fitness equipment by a first prescribed angular offset and (b) a second signal to the second laser device to alter a representation of the second light beam produced by the second laser device in response to the controller detecting, from signaling from the one or more tilt switches, a deviation in lateral movement of the fitness equipment by a second prescribed angular offset.

18. The exercise monitoring apparatus of claim 8,
wherein the fitness equipment comprises a cylindrical bar; and
wherein the fastening member comprises a coiled spring having a first diameter when placed in a first state and securely coupled to the cylindrical bar and having a second diameter when placed in a second state that allow removal of the cylindrical bar.

* * * * *